United States Patent [19]

Iinuma

[11] Patent Number: 4,771,786
[45] Date of Patent: * Sep. 20, 1988

[54] ULTRASONIC METHOD AND APPARATUS FOR TISSUE CHARACTERIZATION AND IMAGING OF NONLINEAR PARAMETER

[75] Inventor: Kazuhiro Iinuma, Nishi-Nasuno, Japan

[73] Assignee: Kabushiki Kaisha Toshiba, Tokyo, Japan

[*] Notice: The portion of the term of this patent subsequent to May 12, 2004 has been disclaimed.

[21] Appl. No.: 23,625

[22] Filed: Mar. 9, 1987

Related U.S. Application Data

[63] Continuation of Ser. No. 748,932, Jun. 26, 1985, Pat. No. 4,664,123.

[30] Foreign Application Priority Data

Jun. 26, 1984 [JP] Japan ............................... 59-131685

[51] Int. Cl.⁴ ............................................. A61B 10/00
[52] U.S. Cl. .................................. 128/660.06; 73/602
[58] Field of Search .................. 128/660; 73/597, 599, 73/602

[56] References Cited

U.S. PATENT DOCUMENTS 4,566,460  1/1986  Sato et al. .......................... 128/660
4,664,123  5/1987  Iinuma ................................ 128/660

Primary Examiner—Francis J. Jaworski
Attorney, Agent, or Firm—Finnegan, Henderson Farabow, Garrett and Dunner

[57] ABSTRACT

A method and apparatus for tissue characterization and imaging of nonlinear parameter data include an array of ultrasonic transducer elements to transmit ultrasonic pulses along a beam toward the tissue and to receive echoes of the ultrasonic pulses. The ultrasonic transducer elements are driven so that the ultrasonic pulses are transmitted at different power levels. The echoes of the ultrasonic pulses are analyzed at each of the different power levels to obtain the nonlinear parameter data along the beam. The beam is scanned in a two-dimensional plane of the tissue. The nonlinear parameter data is displayed according to the two-dimensional plane.

13 Claims, 4 Drawing Sheets

ULTRASONIC METHOD AND APPARATUS FOR TISSUE CHARACTERIZATION AND IMAGING OF NONLINEAR PARAMETER

This is a continuation of application Ser. No. 748,932 filed June 26, 1985 now U.S. Pat. No. 4,664,123.

BACKGROUND OF THE INVENTION

1. Field of the Invention

The present invention relates to an ultrasonic method and apparatus for tissue characterization and imaging of a quantity relating nonlinear parameter B/A. The nonlinear effect arises from characteristics resulting from pressure dependence of sound velocity. The present invention is expected to be sensitive to changes in the detailed structures and properties of tissue and useful in early diagnosis of disease, such as cancer.

2. Prior Art

Ichida et al., *Real Time Nonlinear Parameter Tomography* in Proceeding for 43rd Convention of the Japan Society of Ultrasonics in Medicine, p. 519 (1983) discloses a method in which the changes in the velocity of sound are measured by applying pump waves. In this method, an impulsive relatively high power pumping wave is applied from perpendicular direction to the continuous low intensity probing wave of high frequency so that the phase of the probing wave is modulated instantly by the product of the nonlinear parameter B/A and the pressure of the pumping wave. The resulting modulated probing wave is detected and demodulated to derive the distribution of nonlinear parameter B/A along the probing beam. The processes are repeated by shifting the probing beam to obtain a two-dimensional image. This method, however, is limited to a small or projecting tissue because the pumping wave must be applied perpendicular to the probing wave. It is impossible to examine an internal tissue like a liver.

Akiyama et al., *A Proposal: Nonlinear Parameter Imaging Method by Pulse Echo System,* in Proceedings for 43rd Convention in Japan Society of Ultrasonics in Medicine, p. 521 (1983), discloses a method in which the second harmonic component generated by nonlinear effects is measured. In this method, the pulse echo signals and their second harmonics are detected. The pressure of ultrasonic wave causes the ultrasonic waves to be modulated. Therefore, their second harmonics indicate the nonlinear parameter B/A. Since the transmission frequency is different from the receiving frequency, obtaining exact data by this method without the correction of the attenuation of the sound field is difficult.

SUMMARY OF THE INVENTION

Accordingly, it is an objective of the invention to provide an ultrasonic method and apparatus for characterization of the structure of an object being examined by nonlinear parameter B/A.

It is also an objective of the invention to provide an ultrasonic method and apparatus for in vivo tissue characterization by nonlinear parameter B/A without the correction of the attenuation of the sound field.

It is another objective of the invention to provide an ultrasonic method and apparatus for imaging a quantity relating nonlinear parameter B/A of tissue in real time.

It is still another objective of the invention to provide an ultrasonic method and apparatus for imaging a quantity relating nonlinear parameter B/A of tissue in addition to B-mode imaging of it.

Additional objectives and advantages of the present invention will be set forth in part in the description that follows and in part will be obvious from the description or may be learned by practice of the invention. The objects and advantages of the invention may be realized by the apparatus as particularly pointed out in the appended claims.

To achieve the foregoing objectives and in accorance with the purpose of the invention, as embodied and broadly described herein, the ultrasonic method and apparatus of the present invention comprises an ultrasonic transducer for transmitting ultrasonic pulses along a beam toward an object to be examined and for receiving echoes of the transmitted pulses reflected from discontinuities in the structure of the object along the beam, a driving circuit for transmitting different power levels of the ultrasonic pulses from the ultrasonic transducer, and an arithmetic logic unit for analyzing amplitudes of the echoes against the different power levels of the ultrasonic pulses to obtain nonlinear factor of the structure of the object.

The accompanying drawings, which are incorporated in and constitute part of the specification, illustrate the preferred embodiments of the invention and, together with the description, serve to explain the principles of the invention.

DESCRIPTION OF THE PREFERRED EMBODIMENTS

Reference will now be made in detail to a presently preferred embodiment of the present invention, an example of which is illustrated in the accompanying drawings.

Figure 1:
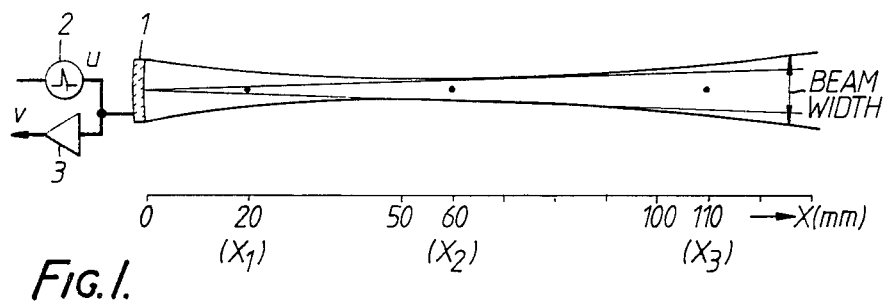
FIG. 1 illustrates an ultrasonic beam pattern propagating in water.
Figure 2:
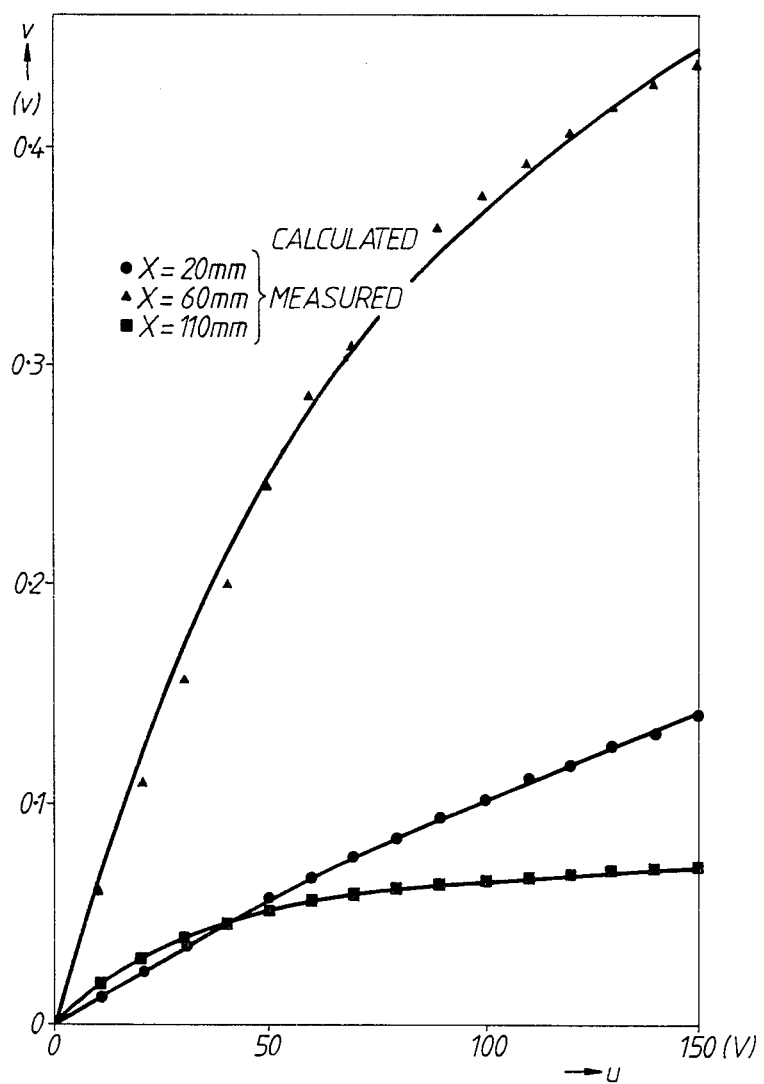
FIG. 2 shows measured values and calculated curves which indicate the nonlinear effect.

In accordance with the present invention, it is understood that the nonlinearity of ultrasonic waves is generally identified with the phenomenon that sound velocity increases in proportion to sound pressure. The more prominent the nonlinear characteristic of the ultrasonic wave, the more harmonic components of ultrasonic wave will be generated. As illustrated in FIGS. 1 and 2, the fundamental component, excluding the harmonic components, tends to be saturated as the sound pressure rises.

FIG. 1 shows the width of an ultrasonic pulse beam from a rectangular transducer 1 with an aperture of 12 mm, frequency of 3.75 MHz and focal distance of 60 mm. A pulser 2 applies a pulse voltage u to the transducer 1, which transmits ultrasonic pulses in water in the direction of three steel wire targets having a diameter of 30 $\mu$m and being positioned at distance $X_1$ (20 mm), distance $X_2$ (60 mm) and distance $X_3$ (110 mm), respectively, from the transducer 1. The transducer 1 receives the echoes reflected from these targets. The output voltage v corresponding to the received echo is obtained through a preamplifier 3.

FIG. 2 shows the relationship between the pulser voltage u, on the one hand, and the output voltages v corresponding to the ultrasonic waves reflected from the wire targets $X_1$, $X_2$ and $X_3$, on the other hand. FIG. 2 may therefore be understood to indicate the nonlinearity of water propagating therein. The echoes reflected farther from the transducer are affected by the nonlinearity of water more strongly due to the effect of integration. Since the echoes reflected from the target positioned at the focal point (60 mm from the transducer 1) are strongest, the nonlinear effect at this point is more prominent than at any other point. Sound beam becomes divergent as the waves propagate farther from the focal point, and the echoes reflected from any point farther than the focal point are weaker. Since the nonlinear effect is integrated through wave propagation path, the stronger nonlinearity of water is observed in order of the echoes reflected from the wire target X3 to the wire target X2, and then to the wire target X1.

The relation between the pulse voltage u and the output voltage v of the preamplifier may be given by the following approximate equation (1):

$$v = \frac{ku}{1 + au} \quad (1)$$

k and a in equation (1) are estimated from the experimental data by the least squares method. The results are as shown in the following table:

| x (mm) | 20 | 60 | 110 |
|---|---|---|---|
| k ($\times 10^{-3}$) | 1.25 | 7.42 | 2.17 |
| a ($\times 10^{-3}$) | 2.19 | 9.91 | 24.90 |

When the values given in the table are substituted for k and a of equation (1), the solid curves as shown in FIG. 2 are obtained. These curves substantially meet with the values given by the experiments.

The above mentioned results are obtained when a propagation medium is water. Similar results may be obtained when ultrasonic waves propagating through tissue of a living body. That is, such curves can be obtained by transmitting ultrasonic pulses into tissue, receiving the echoes reflected from it, and by measuring the amplitudes of the echoes while varying the pulse voltage u, i.e., power of ultrasonic pulses.

Even if the pulse voltage is varied, the sound field and the reflectance of the tissue for the fundamental frequency component of signals are scarcely attenuated and hardly changes. Without the nonlinearity of the ultrasonic waves, the pulse voltage u and the preamplifier output v would be completely proportional, and the value of a in equation (1) would be zero. Due to the nonlinearity of the propagation medium, the output v of the preamplifier is not proportional to the pulse voltage u and is likely to be saturated. The change of the sound field and the influence of the reflectance of the tissue will be given in the form of secondary infinitesimal values.

For instance, sixteen ultrasonic pulses are emitted in the same direction one after another by applying different pulse voltages of 10 v, 20 v . . . 160 v. Hence, the preamplifier generates sixteen output voltages v which correspond to the pulses reflected from points in the tissue. The values for k and a with respect to each point can be calculated from these output voltages v.

More specifically, the preamplifier output v obtained by scanning one line in one direction is sampled at 256 points, for example, and is thus converted into digital data. As a result, k and a for every sampling point are calculated. Value k is concerned with the amplitude of the echoes, and value a is related to nonlinearity. The nonlinear effect is integrated while the ultrasonic waves propagate farther. Hence, the difference between the values a of adjacent sampling points corresponds to the degree of this effect. The nonlinear effect at each point can therefore be understood when the distribution of these differences is displayed on a monitor.

Figure 3:
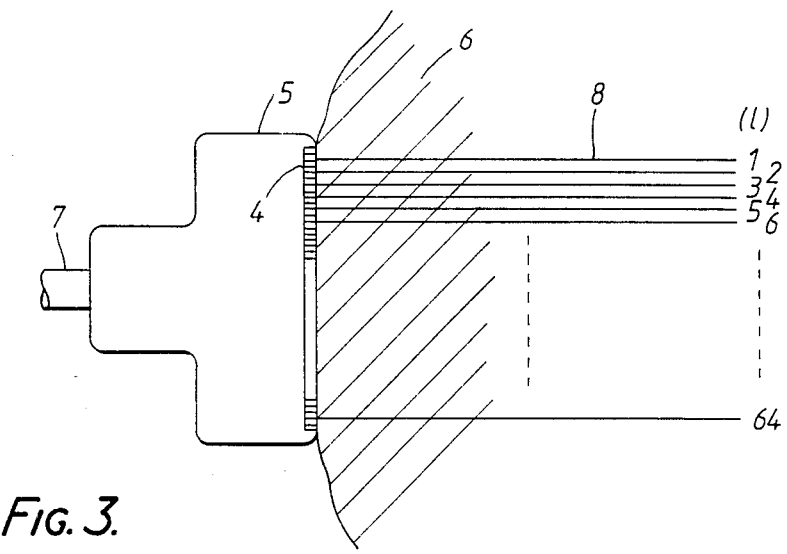
FIG. 3 illustrates principles of electronic linear scanning.

With reference to FIG. 3, it will be briefly explained how an ultrasonic diagnosing apparatus operates to provide a B-mode image by electronic linear scanning. A probe 5 including an array of transducer elements 4 is put on a surface portion of an object 6. Electric pulses are supplied to a first group of adjacent transducer elements 4 through a cable 7. The first group of transducer elements 4 transmits ultrasonic pulses along the first scanning line 8 (l=1). The ultrasonic pulses reflected from the tissues within the object 6 are received by the same group of transducers 4. Echo signals corresponding to the echoes are processed.

As a result, the signals for the scanning line 8 are displayed on a monitor, the brightness of the displayed signal being modulated by the amplitudes of the signals. The next group of transducer elements 4 emit ultrasonic pulses along the second scanning line 8 (l=2) and receive the ultrasonic echoes reflected from the tissues to display them on the second scanning line in the monitor. The other 62 groups of transducer elements 4 operate in the same manner, whereby other scanning lines (l=3, 4 . . . 64) are displayed on the display. The lines (l=1, 2 . . . 64) form a two-dimensional tomogram (i.e., a B-mode image) of the tissue.

Figure 4:
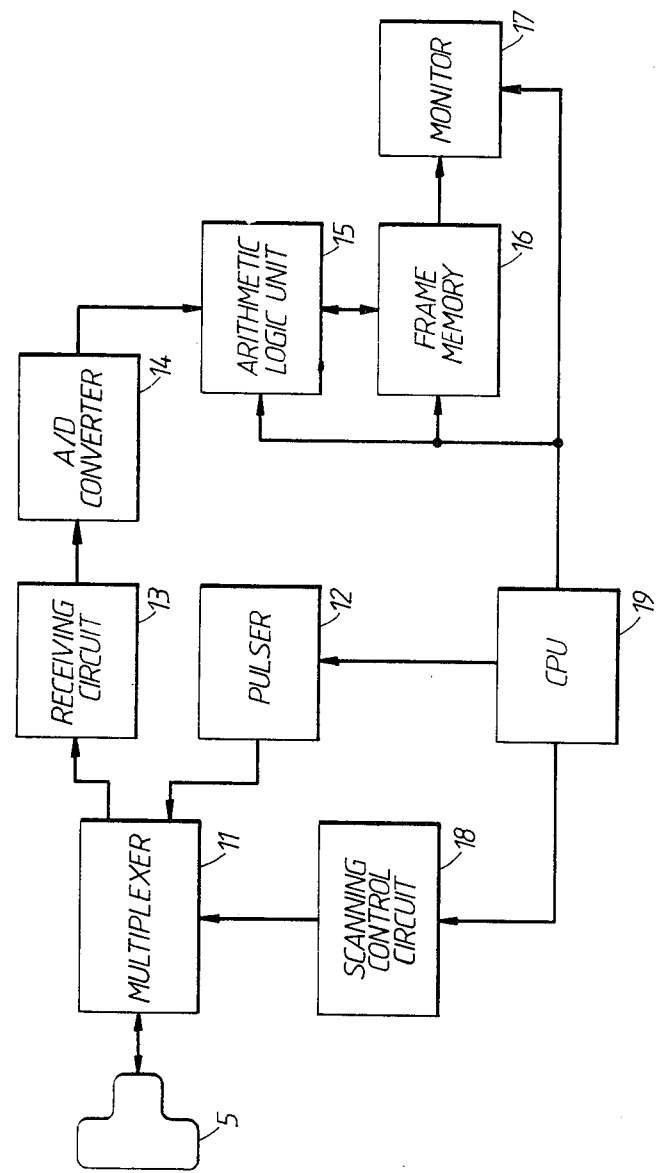
FIG. 4 illustrates a block diagram according to the present invention.

The apparatus according to the present invention will be now described with reference to FIG. 4. The apparatus has a probe 5 including an array of transducer elements 4, which are of the same electronic linear scanning type as shown in FIG. 3. The apparatus comprises a multiplexer 11 which drives a selected group of transducer elements within the array. A pulser 12 is provided to supply pulse voltage u to the transducer elements 4 selected by the multiplexer 11 and to excite the transducer elements in order to transmit ultrasonic pulses to the object. The pulser 12 varies the pulse voltage u to excite the transducer elements.

The apparatus further comprises a receiving circuit 13, an A/D converter 14, an arithmetic logic unit (ALU) 15, a frame memory 16, and a display 17. The receiving circuit 13 receives and detects the signals corresponding to the echoes reflected from tissue in the tested object after being received by the selected transducer elements 4. The A/D converter 14 converts the output signals of the receiving circuit 14 into digital signals. The ALU 15 receives the output signals from the A/D converter 14 and calculates, for example, k and a in expression (1). The ALU 15 will later be described in detail. The frame memory 16 stores signals for each scanning line to form a B-mode image. It also stores the values k and a for each scanning line, which have been calculated by the ALU 15. The monitor 17 displays the values k and a for all scanning lines l stored in the memory 16, as well as the B-mode image formed by the data stored in the memory 16.

The apparatus further includes a scanning control circuit 18 and a CPU 19. The circuit 18 controls the switching of the transducer elements 4 of the probe 5. The CPU 19 is responsible for feeding various signals throughout the apparatus. It feeds switching control signals to the circuit 18, a rate pulse of the ultrasonic pulses and a voltage control signal to the pulser 12, and control signals to the circuit 15, memory 16 and monitor 17.

The probe 5 and some of the electronic circuits may be used in combination with the apparatus which provides a B-mode image by electronic linear scanning. In this case, a different scanning method must be used, the pulser 12 outputs different signals, and the monitor 17 displays data. The operation of the apparatus will now be described in detail.

First, the pulser 12 generates electric pulses of 10 v. In response to these pulses, selected transducer elements 4 of the probe 5 are excited. These transducer elements 4 transmit ultrasonic pulses along the scanning line 8 (l=1) shown in FIG. 3. The pulses are reflected from the tissue in the object, and echoes of them are received by the same transducer elements 4. The output signals of these transducer elements 4 are supplied to the receiving circuit 13 through the multiplexer 11 and are amplified by the circuit 13. The A/D converter 14 converts the output signals of the circuit 13 to digital signals. The digital signals are input to the high-speed arithmetic logic unit 15. When the clock frequency of the A/D converter 14 is 1 MHz and the sound velocity is 1500 m/s, ultrasonic wave propagates out a distance of 0.75 mm and back through the tissue in about one microsecond. The A/D converter 14 continuously obtains 256 sampled values, to collect data showing the amplitudes of echoes reflected from that portion of the tissue which is 192 mm deep (0.75 mm×256) from the surfaces of the transducers (i.e., the surface of the object). The data, which is obtained, is stored in the frame memory 16. The data corresponds to 256 pixels arranged along a scanning line at intervals of 0.75 mm.

Then, the pulser 12 outputs electric pulses of 20 v, so that ultrasonic wave pulses are emitted along the same scanning line 8 (l=1). The data showing the received waveform is stored in the frame memory 16. Thereafter, the pulser 12 generates electric pulses of 30 v, electric pulses of 40 v . . . and electric pulses of 160 v. When sixteen items of data are obtained, the scanning control circuit 18 selects the next scanning line 8 (l=2). Then, the pulse-transmission and reception are repeated sixteen times along this line 8 (l=2), and along each of the remaining scanning lines 8.

The sixteen items of data obtained by transmitting receiving ultrasonic pulses along the line (l=1) each include data representing the amplitudes of the echoes and consisting of 256 pixels arranged at intervals of 0.75 mm in the direction of depth. Hence, sixteen items of wave amplitude data are provided for each of the 256 points where the ultrasonic echoes are reflected. The high-speed arithmetic logic unit 15 calculates values [kj] and [aj], i.e., k's and a's in equation (1) for all pixels j (1, 2, . . . 256) from the sixteen pulse voltages (10 v, 20 v . . . 160 v) for each point and the sixteen items of wave amplitude data for each point. The values [kj] and [aj] obtained by the circuit 15 are written in the frame memory 16 as data associated with the scanning line (l=1). Values [kj] and [aj] for the other scanning lines (l=2, 3 . . . 64) are also written in the frame memory 16.

The sets of values [kj] and [aj] for all scanning lines 8 (l=1, 2 . . . 64), i.e., data [kj,l] and [aj,l], are read from frame memory 16 and displayed by the monitor 17, whereby a two-dimensional tomogram is formed. When the data [kj,l] is displayed, this image is similar to the ordinary B-mode image. When the data [aj,l] is read out from the memory 16 and displayed on the monitor 17, the display represents the nonlinear parameter B/A of the tissue. When the monitor 17 is a color monitor and the data [kj,l] and [aj,l] are used as a brightness-modulating signals and a color signal, respectively, the data obtained due to the nonlinear effect representing the structures and properties of the tissue can be displayed with the data to denote the shape of the tissue.

When the rate frequency at which pulses are generated is 4 KHz, it takes 16 ms to scan 64 lines (0.75 ms×64) to form an ordinary B-mode image. This embodiment is sixteen times as long as in the ordinary B-mode, i.e., 256 ms or approximately ¼ sec to scan 64 lines. This period of time is sufficiently short from a clinical point of view, particularly for an abdominal examination.

Figure 5:
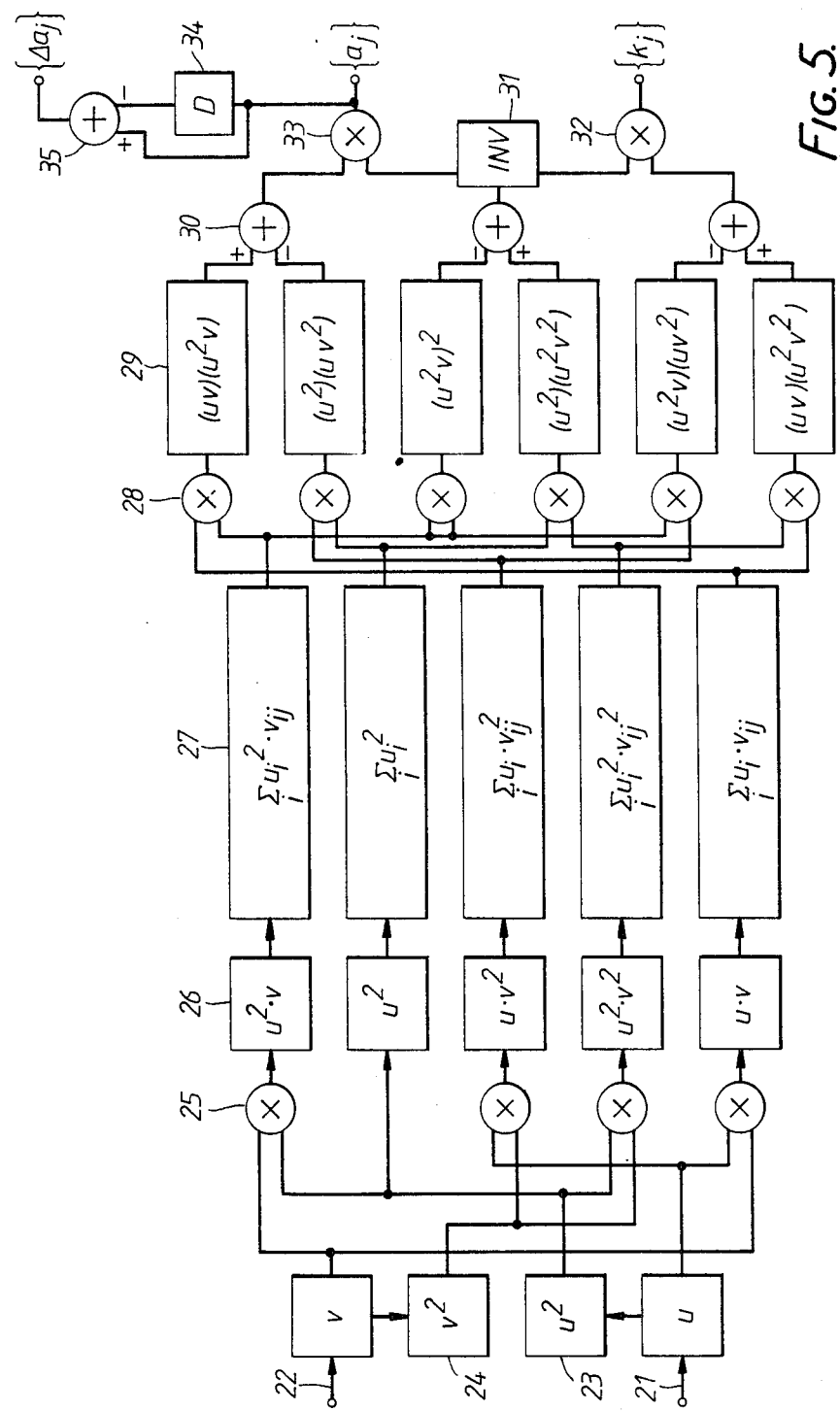
FIG. 5 illustrates a circuit diagram of arithmetic logic unit shown in FIG. 4.

FIG. 5 shows the arithmetic logic unit 15 for calculating [kj,l] and [aj,l]. Digital values u1 (10), u2 (20) . . . , $u_i$ . . . , u16 (160) representing the pulse voltages are input to a pulse voltage input terminal 21. The squares $u_i^2$ of these digital values are given by a conversion table 23. In the meantime, the received voltage v (i.e., the output of the A/D converter 4) is input to a received voltage input terminal 22. This voltage v is converted to value $v^2$ by another conversion table 24. Let vij denote the voltage supplied to the jth pixel when the pulse voltage is ui. The values kj and aj for the jth pixel of the scanning line (l=1), which may be estimated from sixteen pieces of input and output data, ui, vij, (where i=1, 2 . . . 16), are given by the following expressions:

$$k_j = \frac{(\Sigma u_j v_{ij})(\Sigma u_i^2 v_{ij}^2) - (\Sigma u_i^2 v_{ij})(\Sigma u_i v_{ij}^2)}{(\Sigma u_i^2)(\Sigma u_i^2 v_{ij}^2) - (\Sigma u_i^2 v_{ij})^2} \quad (2)$$

$$k_j = \frac{(\Sigma u_j v_{ij})(\Sigma u_i^2 v_{ij}^2) - (\Sigma u_i^2 v_{ij})(\Sigma u_i v_{ij}^2)}{(\Sigma u_i^2)(\Sigma u_i^2 v_{ij}^2) - (\Sigma u_i^2 v_{ij})^2} \quad (3)$$

where $$\Sigma = \frac{\Sigma}{i}.$$

The output 26 of the multiplier 25 shown in FIG. 5 indicates the value obtained before adding the values in the parentheses in expressions (2) and (3), both the numerator and the denominator. When the first pulse is supplied (i=1), the multipliers 25 generate output 26 for 256 pixels (j=1, 2 . . . 256), which are stored in the memories 27. When the second pulse is applied (i=2), the multipliers 25 generate output 26 for 256 pixels (j=1, 2 . . . 256). These outputs 26 are added to the data stored in the memories 27. When the third, fourth . . . and sixteenth pulses are supplied one after another (i=3, 4 . . . 16), the multipliers 25 repeat the same operation, and their outputs 26 are added to the data stored in the memories 27. As a result, the values in the parentheses in expressions (2) and (3) are obtained. The multipliers 28 are used to find the products of these values. The outputs 29 of the multipliers 28 are added or subtracted by adders 30. The reciprocal of the denominator is obtained by a conversion table 31, and multipliers 32 and 33 are used to find the products of the outputs from the adders 30. Consequently, the values for a set of kj and a set of aj, i.e., [kj]=(k1, k2 ... k256) and [aj]=(a1, a2 ... a256), are calculated.

Multiplication and addition can be achieved at a high speed. Therefore, they can be carried out in real time, at the timing of the transmission and reception of ultrasonic waves. These calculations provide [kj] and [aj] for the scanning line (l=1). These values are stored in the frame memory 16. Similarly, [kj] and [aj] for the other scanning lines (l=2, 3 ... 64) are obtained and stored in the frame memory 16. Hence, the memory 16 stores data representing the values of k and a for any of 256×64 pixels forming a two-dimensional tomogram. The time for obtaining the data is about ¼ second, as mentioned above. The data is read from the frame memory 16 at the rate of 30 frames per second, and a tomogram is displayed by the display 17.

The nonlinear effect is identified with the integration effect in the depth direction from the body surface. In practice, it is desirable that the value for a be differentiated in the depth direction. Alternatively the difference [$\Delta$aj] between [aj] and the output [aj-1] of a one-pixel delay circuit 34 are outputed, and image data [$\Delta$aj,l] are transferred to the frame memory 16 and then displayed.

As described earlier, the data is provided by varying the pulse voltage to 10 v, 20 v ... and finally to 160 v. The lower the pulse voltage, the lower the voltage corresponding to the amplitudes of the echoes. Hence, the signal-to-noise (S/N) ratio of the received signal is inversely proportional to the pulse voltage. Therefore, when the pulse voltage is low, many items of data should be provided so that their sum or average may be used.

In view of the scanning direction (l=1), the pulse voltage of 10 v from the pulser 12, which is triggered by 4 KHz rate pulses, is used 256 times, i.e. $(160/10)^2$, the pulse voltage of 20 v is used 64 times, i.e. $(160/20)^2$, the pulse voltage of 30 v is used 28 times, i.e. $(160/30)^2$, and so forth. Hence, the pulse voltage 160 v is used only once.

The received signals corresponding to each pulse voltage are added, and their average value used as vij. When addition is repeated N times, the signal component grows N times, while the random noise also increase N times. As a result, the S/N ratios are substantially equal despite the different pulse voltages.

Figure 6:
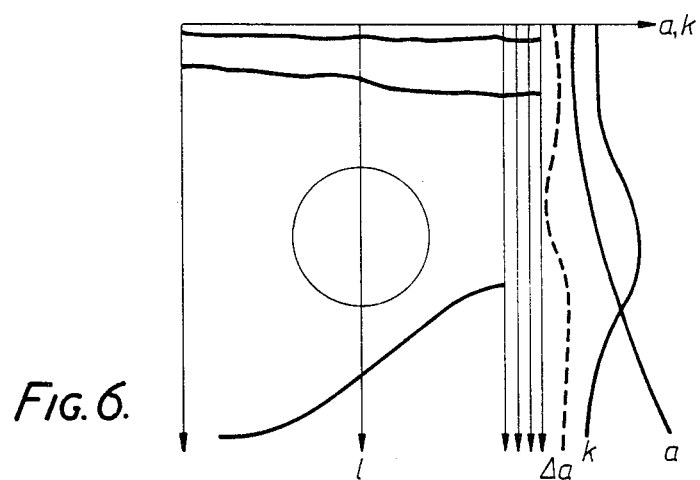
FIG. 6 illustrates another embodiment according to the present invention.

In this case, to calculate [kj], [aj] or [$\Delta$aj] for one scanning line, 402 rate pulses (i.e., 256+64+28+ ... +1) must be applied. If the rate frequency is 4 KHz, it takes about 0.1 sec. to calculate this value. This does not matter in the case of an abdominal examination. In examining the abdomen, the scanning lines are aligned with the area of interest, and the values of [kj], [aj] and [$\Delta$aj] on these lines may be displayed together with the tomogram, in such a manner as illustrated in FIG. 6.

As described above, the present embodiment of the invention has the following advantages:

(1) The transducer elements 4 transmit ultrasonic pulses of the same frequency and different amplitudes. Neither the sound field nor the pulse waveform is distorted, and the nonlinearity due to the different amplitudes of the pulses is correctly observed. Hence, the sound field need not be corrected to compensate for the difference in amplitudes between the ultrasonic pulses.

(2) The ordinary pulse reflection techniques can be used in the embodiment of the invention. Therefore, the probe and some of the circuits may be the same as those conventionally used in ultrasonic diagnostic apparatus. Moreover, the embodiment is easy to operate and can provide, in a short time, the great deal of data required to obtain a two-dimensional tomogram.

(3) The known ultrasonic diagnostic apparatus, which provides a B-mode image, is used chiefly to ascertain the shape of living tissue. The embodiment of this invention provides data representing the structures and properties of the tissue. When the apparatus is used together with the known apparatus by providing B-mode image the tissue can be characterized, which was impossible with the known apparatus alone.

(4) Parameter a, which represents the nonlinear effect, contains data showing the velocity at which ultrasonic waves propagate. It is possible to evaluate the hardness and fat lubrication of the tissue, e.g., the tissue of liver.

As above mentioned, the embodiment of the present invention can provide the nonlinear parameters of the tissue non-invasively, unlike the conventional apparatus. It can obtain parameter data represeting nonlinear effects at ten thousand or more points very easily, within one second. The data can be two-dimensionally displayed together with a B-mode image (i.e., anatomical data). In view of this, the present invention provides a new method of ultrasonic diagnosis.

The present invention is not limited to the above embodiment which is designed to perform electronic linear scanning. It may be applied to a method using single transducers or the electronic sector scanning or other scanning methods.

Usually, each transducer transmits ultrasonic pulses and then receives echoes of them. Instead, two transducers may be used, one to transmit ultrasonic waves, and the other to receive echoes of them. This holds true not only for the pulse reflection method but also for the pulse transmission method or burst wave (or continuous waves) transmission method.

The number of scanning lines is not limited to 64, and the number of pixels is not necessarily 256.

Further, the parameters representing the nonlinear effect may be calculated not only in accordance with expression (1), but also with any other expression that well expresses this effect.

Moreover, the values for compensating for the effect of the sound field, for compensating for the attenuation made by tissue, and for compensating for the effect of the frequency used may be added to a in equation (1) or to the value obtained by differentiating a. If a frequency of 2 MHz is used, the attenuation is not very prominent and is simple.

It will be apparent to those skilled in the art that modifications and variations can be made to the method and apparatus of the present invention. The invention in its broader aspects is, therefore, not limited to the specific details, representative apparatus, and illustrative examples shown and described. Thus, it is intended that all matter contained in the foregoing description or shown in the accompanying drawings be interpreted as illustrative and not in a limiting sense.

What is claimed is:

1. An ultrasonic method for characterization by nonlinear parameter data of a structure of an object to be examined which comprises the steps of:

transmitting ultrasonic pulses along a line extending into the object at a plurality of different output power levels;

receiving a plurality of echoes of said ultrasonic pulses reflected from discontinuities in the structure at discrete points along the line; and analyzing amplitudes of said received echoes at each of said different output power levels to obtain data relating to the nonlinear parameter B/A of the structure.

2. An ultrasonic apparatus for characterization by nonlinear parameter data of a structure of an object to be examined comprising:

ultrasonic transducer means for transmitting when activated ultrasonic pulses along a beam line extending into the object and for receiving a plurality of echoes of said ultrasonic pulses reflected from discontinuities in the structure at discrete points along the line;

driving means for activating said transducer means at a plurality of different power levels; and means for analyzing amplitudes of said echoes at each of said different power levels to obtain data relating to the nonlinear parameter B/A of the structure.

3. An apparatus for characterization and imaging by nonlinear parameter data of a structure of an object to be examined comprising:

an array of ultrasonic transducer elements arranged in a first dimension, each transducer element to transmit when activated ultrasonic pulses along a line extending into the object in a second dimension and to receive echoes of said ultrasonic pulses from discrete points along said line;

means for activating said ultrasonic transducer elements at a plurality of different power levels;

means for analyzing amplitudes of said echoes for each of said transducer elements arranged in said first dimension at each of said different power levels to obtain nonlinear parameter data B/A along each of said lines in said second dimension;

means for scanning said data obtained in said first and second dimensions; and means responsive to said scanning means for displaying said nonlinear parameter data in two dimensions.

4. The apparatus according to claim 3 wherein said activating means includes means for varying voltages u activating said transducer elements and wherein said transducer elements include means for converting said received echoes into voltages v.

5. An apparatus for characterization and imaging by nonlinear parameter data of a structure of an object to be examined comprising:

an array of ultrasonic transducer elements arranged in a first dimension, each transducer element to transmit when activated ultrasonic pulses along a line extending into the object in a second dimension and to receive echoes of said ultrasonic pulses from discrete points along said line;

means for activating said ultrasonic transducer elements at a plurality of different power levels;

means for analyzing amplitudes of said echoes for each of said transducer elements arranged in said first dimension at each of said different power levels to obtain nonlinear parameter data B/A along each of said lines in said second dimension; and means responsive to said analyzing means for displaying said nonlinear parameter data in two dimensions;

wherein said activating means includes means for varying voltages u activating said transducer elements;

wherein said transducer elements include means for converting said received echoes into voltages v; and wherein said means for analyzing comprises means for calculating linear parameter data k and nonlinear parameter data a for each of said discrete points according to the equation:

$$v = \frac{k \cdot u}{1 + a \cdot u}.$$

6. The apparatus according to claim 5 wherein said displaying means includes means for displaying said amplitude data k in two dimensions.

7. The apparatus according to claim 5 wherein said displaying means includes means for displaying said amplitude k in a gray scale and for displaying said nonlinear parameter data a in a colored scale.

8. An apparatus for characterization and imaging by nonlinear parameter date of a structure of an object to be examined, comprising:

(a) an array of ultrasonic transducers arranged in a first dimension, each transducer transmitting, when activated, ultrasonic pulses in a predetermined line extending into said object in a second dimension, each transducer receiving echoes of the pulses being reflected from discontinuities in the structure along the predetermined line;

(b) a driving circuit for activating each of said transducers at a plurality of different power levels;

(c) means for sampling echoes received by each transducer at a frequency corresponding to the time calculated for sound to theoretically travel from each transducer to a discrete set of points along said line and back again through said object;

(d) an arithmetic logic unit for calculating a linear parameter B/A representative of the pressure dependence of sound velocity for each of said discrete points using amplitudes of echoes sampled at each of said different power levels; and (e) means responsive to said logic unit means for displaying, in two dimensions, parameters calculated for each discrete point of each line.

9. An apparatus according to claim 8 wherein said driving circuit includes means for varying voltages u activating said transducer elements, and wherein said transducer elements include means for converting said received echoes into voltages v.

10. An apparatus according to claim 9 wherein said arithmetic logic unit comprises means for calculating linear parameter data k and nonlinear parameter data a for each of said discrete points according to the equation:

$$v = \frac{k \cdot u}{1 + a \cdot u}.$$

11. An apparatus according to claim 10, wherein said means for displaying includes means for displaying nonlinear parameter a for each discrete point.

12. An apparatus according to claim 10 wherein said means for displaying includes means for displaying both the nonlinear parameter a and linear parameter k for each discrete point.

13. An apparatus according to claim 11 wherein said means for displaying includes means for displaying parameter k in a gray scale and parameter a in a color scale.

* * * * *